(12) United States Patent
Chavan et al.

(10) Patent No.: US 12,697,426 B2
(45) Date of Patent: Aug. 4, 2026

(54) VACUUM SYSTEM TO CLEAR STANDING COLUMN OF FLUID

(71) Applicant: C. R. Bard, Inc., Franklin Lakes, NJ (US)

(72) Inventors: Varad Chavan, Kolhapur (IN); Rohit Sinha, Lawrenceville, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 18/274,157

(22) PCT Filed: Jan. 13, 2022

(86) PCT No.: PCT/US2022/012373
§ 371 (c)(1),
(2) Date: Jul. 25, 2023

(87) PCT Pub. No.: WO2022/159333
PCT Pub. Date: Jul. 28, 2022

(65) Prior Publication Data
US 2025/0025617 A1      Jan. 23, 2025

Related U.S. Application Data

(60) Provisional application No. 63/141,302, filed on Jan. 25, 2021.

(51) Int. Cl.
*A61M 1/00* (2006.01)
*A61F 5/44* (2006.01)

(52) U.S. Cl.
CPC ............. *A61M 1/74* (2021.05); *A61F 5/4405* (2013.01); *A61M 1/70* (2021.05)

(58) Field of Classification Search
CPC .. A61M 1/74; A61M 1/70; A61M 2210/1085; A61M 2202/0496; A61M 25/0017; A61M 1/60; A61M 1/63
See application file for complete search history.

(56) References Cited

U.S. PATENT DOCUMENTS

| | | | |
|---|---|---|---|
| 3,114,916 A | 12/1963 | Hadley | |
| 3,583,401 A | 6/1971 | Vailiancourt et al. | |
| 3,598,124 A | 8/1971 | Andersen et al. | |
| | (Continued) | | |

FOREIGN PATENT DOCUMENTS

| | | | |
|---|---|---|---|
| CN | 106955208 A | * | 7/2017 |
| CN | 116650740 A | * | 8/2023 |
| | (Continued) | | |

OTHER PUBLICATIONS

PCT/US2020/066707 filed Dec. 22, 2020 International Search Report and Written Opinion dated Apr. 15, 2021.
(Continued)

*Primary Examiner* — Adam Marcetich
(74) *Attorney, Agent, or Firm* — Rutan & Tucker LLP

(57) ABSTRACT

A vacuum system can include a vacuum chamber in fluid communication with each of a catheter, a suction tube, and a fluid collecting bag. The vacuum chamber can include a proximal opening covered by a lid, a lateral opening coupled to a first drainage tube configured to receive a volume of fluid, and a distal opening coupled to a proximal opening of a valve.

28 Claims, 6 Drawing Sheets

(56) References Cited

U.S. PATENT DOCUMENTS

| | | | |
|---|---|---|---|
| 3,661,143 A | 5/1972 | Henkin | |
| 3,707,972 A | 1/1973 | Villari et al. | |
| 3,861,394 A | 1/1975 | Villari | |
| 3,901,235 A | 8/1975 | Patel et al. | |
| 3,955,574 A | 5/1976 | Rubinstein | |
| 4,013,076 A | 3/1977 | Puderbaugh et al. | |
| 4,084,593 A | 4/1978 | Jarund | |
| 4,250,872 A | 2/1981 | Tamari | |
| 4,265,243 A | 5/1981 | Taylor | |
| 4,266,689 A | 5/1981 | Asher | |
| 4,305,403 A | 12/1981 | Dunn | |
| 4,315,506 A | 2/1982 | Kayser et al. | |
| 4,360,933 A | 11/1982 | Kimura et al. | |
| 4,465,485 A | 8/1984 | Kashmer et al. | |
| 4,490,144 A | 12/1984 | Steigerwald | |
| 4,531,939 A | 7/1985 | Izumi | |
| 4,556,997 A | 12/1985 | Takamiya et al. | |
| 4,631,061 A | 12/1986 | Martin | |
| 4,654,029 A | 3/1987 | D'Antonio | |
| 4,711,365 A | 12/1987 | Fomby | |
| 4,747,166 A * | 5/1988 | Kuntz | A61F 5/455 |
| | | | 4/144.1 |
| 4,810,242 A | 3/1989 | Sundblom et al. | |
| 4,819,684 A | 4/1989 | Zaugg et al. | |
| 4,872,579 A | 10/1989 | Palmer | |
| 4,880,411 A | 11/1989 | Fangrow, Jr. et al. | |
| 4,990,137 A | 2/1991 | Graham | |
| 5,002,528 A | 3/1991 | Palestrant | |
| 5,071,411 A | 12/1991 | Hillstead | |
| 5,100,376 A * | 3/1992 | Blake, III | A61M 1/02 |
| | | | 604/320 |
| 5,186,431 A | 2/1993 | Tamari | |
| 5,242,404 A | 9/1993 | Conley et al. | |
| 5,318,550 A | 6/1994 | Cermak et al. | |
| 5,359,233 A | 10/1994 | Mumper et al. | |
| 5,405,319 A | 4/1995 | Abell et al. | |
| RE35,707 E | 12/1997 | Takamiya et al. | |
| 5,738,656 A | 4/1998 | Wagner et al. | |
| 5,813,842 A | 9/1998 | Tamari | |
| 5,894,608 A | 4/1999 | Birbara | |
| 6,007,521 A | 12/1999 | Bidwell et al. | |
| 6,106,506 A | 8/2000 | Abell et al. | |
| 6,183,454 B1 | 2/2001 | Levine et al. | |
| 7,833,186 B1 | 11/2010 | Batiste | |
| 8,266,741 B2 | 9/2012 | Penninger et al. | |
| 8,337,475 B2 | 12/2012 | Christensen et al. | |
| 8,366,692 B2 | 2/2013 | Weston et al. | |
| 8,475,419 B2 | 7/2013 | Eckermann | |
| 8,512,301 B2 | 8/2013 | Ma | |
| 9,814,866 B1 | 11/2017 | Goswami | |
| 10,363,184 B2 | 7/2019 | Zerhusen et al. | |
| 10,391,275 B2 | 8/2019 | Burnett et al. | |
| 10,426,919 B2 | 10/2019 | Erbey, II et al. | |
| 10,506,965 B2 | 12/2019 | Cooper et al. | |
| 10,737,057 B1 | 8/2020 | Mikhail et al. | |
| 10,772,998 B2 | 9/2020 | Luxon et al. | |
| 12,097,150 B2 | 9/2024 | Chancy et al. | |
| 2002/0000253 A1 | 1/2002 | Fillmore et al. | |
| 2002/0087131 A1 * | 7/2002 | Wolff | A61B 5/20 |
| | | | 604/327 |
| 2002/0161317 A1 | 10/2002 | Risk et al. | |
| 2003/0078638 A1 | 4/2003 | Voorhees et al. | |
| 2004/0176746 A1 | 9/2004 | Forral | |
| 2004/0230181 A1 | 11/2004 | Cawood | |
| 2004/0236292 A1 | 11/2004 | Tazoe et al. | |
| 2004/0254547 A1 | 12/2004 | Okabe et al. | |
| 2005/0183780 A1 | 8/2005 | Michaels et al. | |
| 2005/0197647 A1 | 9/2005 | Dolliver et al. | |
| 2005/0209585 A1 | 9/2005 | Nord et al. | |
| 2005/0245898 A1 | 11/2005 | Wright et al. | |
| 2005/0256460 A1 | 11/2005 | Rome et al. | |
| 2005/0261619 A1 | 11/2005 | Gay | |
| 2006/0015190 A1 | 1/2006 | Robertson | |
| 2006/0079854 A1 * | 4/2006 | Kay | A61F 5/4405 |
| | | | 604/328 |
| 2006/0155260 A1 | 7/2006 | Blott et al. | |
| 2006/0213527 A1 * | 9/2006 | Argenta | A61B 90/00 |
| | | | 128/898 |
| 2006/0235353 A1 | 10/2006 | Gelfand et al. | |
| 2006/0270971 A1 | 11/2006 | Gelfand et al. | |
| 2006/0271019 A1 | 11/2006 | Stoller et al. | |
| 2007/0005002 A1 | 1/2007 | Millman et al. | |
| 2007/0078444 A1 | 4/2007 | Larsson | |
| 2007/0142729 A1 | 6/2007 | Pfeiffer et al. | |
| 2007/0272311 A1 | 11/2007 | Trocki et al. | |
| 2008/0051708 A1 * | 2/2008 | Kumar | A61M 1/74 |
| | | | 604/119 |
| 2008/0156092 A1 | 7/2008 | Boiarski | |
| 2008/0281254 A1 | 11/2008 | Humayun et al. | |
| 2008/0312550 A1 | 12/2008 | Nishtala et al. | |
| 2009/0076469 A1 | 3/2009 | Alexandersen | |
| 2009/0157016 A1 | 6/2009 | Adahan | |
| 2009/0157040 A1 | 6/2009 | Jacobson et al. | |
| 2009/0326483 A1 | 12/2009 | Green | |
| 2010/0042059 A1 * | 2/2010 | Pratt | A61M 1/96 |
| | | | 700/282 |
| 2010/0106116 A1 | 4/2010 | Simmons et al. | |
| 2010/0130949 A1 | 5/2010 | Garcia | |
| 2010/0280435 A1 * | 11/2010 | Raney | A61M 1/76 |
| | | | 604/35 |
| 2011/0060300 A1 * | 3/2011 | Weig | A61F 5/451 |
| | | | 604/319 |
| 2012/0036638 A1 | 2/2012 | Penninger et al. | |
| 2012/0323144 A1 | 12/2012 | Coston et al. | |
| 2013/0218106 A1 | 8/2013 | Coston et al. | |
| 2014/0053841 A1 | 2/2014 | Ratner | |
| 2014/0200558 A1 | 7/2014 | McDaniel | |
| 2014/0200588 A1 | 7/2014 | Anderson et al. | |
| 2014/0276497 A1 * | 9/2014 | Robinson | A61M 1/882 |
| | | | 604/319 |
| 2015/0126975 A1 | 5/2015 | Wuthier | |
| 2015/0141957 A1 * | 5/2015 | Hauswald | A61M 5/31548 |
| | | | 604/152 |
| 2015/0290448 A1 | 10/2015 | Pavlik | |
| 2016/0135982 A1 | 5/2016 | Garcia | |
| 2016/0183819 A1 | 6/2016 | Burnett et al. | |
| 2016/0310711 A1 * | 10/2016 | Luxon | A61B 5/208 |
| 2017/0014560 A1 | 1/2017 | Minskoff et al. | |
| 2017/0014617 A1 * | 1/2017 | Huici | A61M 39/24 |
| 2017/0072125 A1 | 3/2017 | Wallenås et al. | |
| 2017/0136209 A1 * | 5/2017 | Burnett | A61M 1/84 |
| 2017/0143566 A1 | 5/2017 | Elku et al. | |
| 2017/0209630 A1 * | 7/2017 | Klusmann | A61M 1/984 |
| 2017/0241978 A1 | 8/2017 | Duval | |
| 2017/0312114 A1 | 11/2017 | Glithero | |
| 2018/0015251 A1 | 1/2018 | Lampotang et al. | |
| 2018/0071441 A1 | 3/2018 | Croteau et al. | |
| 2018/0104391 A1 | 4/2018 | Luxon et al. | |
| 2018/0110456 A1 | 4/2018 | Cooper et al. | |
| 2018/0125697 A1 | 5/2018 | Ferrera | |
| 2018/0177458 A1 | 6/2018 | Burnett et al. | |
| 2018/0185222 A1 | 7/2018 | Zerhusen et al. | |
| 2018/0235523 A1 | 8/2018 | Sauder | |
| 2018/0245699 A1 | 8/2018 | Lee | |
| 2018/0360424 A1 | 12/2018 | Yurek et al. | |
| 2019/0009021 A1 | 1/2019 | Nelson et al. | |
| 2019/0009023 A1 | 1/2019 | Diperna et al. | |
| 2019/0030264 A1 | 1/2019 | Herskovic et al. | |
| 2019/0038451 A1 | 2/2019 | Harvie | |
| 2019/0046102 A1 | 2/2019 | Kushnir et al. | |
| 2019/0126006 A1 | 5/2019 | Rehm et al. | |
| 2019/0143008 A1 * | 5/2019 | Brundage | A61M 1/74 |
| | | | 604/30 |
| 2019/0143094 A1 | 5/2019 | DeMeritt | |
| 2019/0151610 A1 | 5/2019 | Fletter | |
| 2019/0175801 A1 * | 6/2019 | Levine | A61M 1/062 |
| 2019/0255242 A1 | 8/2019 | Cull | |
| 2019/0343445 A1 | 11/2019 | Burnett et al. | |
| 2020/0000979 A1 | 1/2020 | Myers | |
| 2020/0061281 A1 | 2/2020 | Desouza et al. | |
| 2020/0155751 A1 | 5/2020 | Batiste | |
| 2020/0315837 A1 | 10/2020 | Radl et al. | |
| 2021/0077007 A1 | 3/2021 | Jouret et al. | |

(56) References Cited

U.S. PATENT DOCUMENTS

| | | | |
|---|---|---|---|
| 2022/0152345 A1 | 5/2022 | Simiele et al. | |
| 2022/0160949 A1 | 5/2022 | Simiele et al. | |
| 2022/0176031 A1 | 6/2022 | Cheng et al. | |
| 2022/0193366 A1 | 6/2022 | Cheng et al. | |
| 2022/0218890 A1 | 7/2022 | Chavan | |
| 2022/0218973 A1 | 7/2022 | Chavan et al. | |
| 2022/0218974 A1 | 7/2022 | Chavan et al. | |
| 2022/0273213 A1* | 9/2022 | Sokolov | A61B 5/02055 |
| 2022/0287689 A1* | 9/2022 | Johannes | A61F 5/4405 |
| 2022/0305189 A1 | 9/2022 | Chavan et al. | |
| 2022/0330867 A1 | 10/2022 | Conley et al. | |
| 2022/0362080 A1 | 11/2022 | McCorquodale et al. | |
| 2022/0409421 A1* | 12/2022 | Hughett | A61F 5/4408 |
| 2023/0013353 A1 | 1/2023 | Chavan et al. | |
| 2023/0030637 A1 | 2/2023 | Gloeckner et al. | |
| 2023/0054937 A1 | 2/2023 | Chancy et al. | |
| 2023/0083906 A1 | 3/2023 | Jones et al. | |
| 2023/0277199 A1* | 9/2023 | Duffy | A61M 1/774 604/30 |
| 2023/0310837 A1 | 10/2023 | Gamsizlar et al. | |
| 2024/0033404 A1 | 2/2024 | Ishikawa | |
| 2024/0238500 A1 | 7/2024 | Simiele et al. | |
| 2024/0307604 A1 | 9/2024 | Chavan | |
| 2025/0009578 A1 | 1/2025 | Chancy et al. | |
| 2025/0018147 A1 | 1/2025 | Rehm | |
| 2025/0018149 A1 | 1/2025 | Cheng et al. | |
| 2025/0025620 A1 | 1/2025 | Cheng et al. | |
| 2025/0040848 A1 | 2/2025 | Lai et al. | |
| 2025/0177632 A1 | 6/2025 | Jones et al. | |
| 2025/0186735 A1 | 6/2025 | Rehm et al. | |
| 2025/0288775 A1 | 9/2025 | Simiele et al. | |
| 2026/0014310 A1 | 1/2026 | Chavan | |

FOREIGN PATENT DOCUMENTS

| | | | |
|---|---|---|---|
| EP | 1122435 A1 | 8/2001 | |
| EP | 1872752 A1 | 1/2008 | |
| EP | 2417955 A2 | 2/2012 | |
| EP | 2730299 A1 | 5/2014 | |
| EP | 4096611 B1 | 5/2025 | |
| EP | 4585150 A2 | 7/2025 | |
| GB | 1408821 A | 10/1975 | |
| GB | 2235256 | 2/1991 | |
| WO | 2009026237 A1 | 2/2009 | |
| WO | 2012016179 A1 | 2/2012 | |
| WO | 2015019056 A1 | 2/2015 | |
| WO | 2015105916 A1 | 7/2015 | |
| WO | 2016012494 A1 | 1/2016 | |
| WO | 2017177068 A1 | 10/2017 | |
| WO | 2018136306 A1 | 7/2018 | |
| WO | 2018191193 A1 | 10/2018 | |
| WO | 2019004854 A1 | 1/2019 | |
| WO | 2019083104 A1 | 5/2019 | |
| WO | 2020033752 A1 | 2/2020 | |
| WO | 2021154427 A1 | 8/2021 | |
| WO | 2021158332 A1 | 8/2021 | |
| WO | 2022108589 A1 | 5/2022 | |
| WO | 2022159333 A1 | 7/2022 | |
| WO | 2022251425 A1 | 12/2022 | |
| WO | 2023086394 A1 | 5/2023 | |
| WO | 2024118072 A1 | 6/2024 | |
| WO | 2024151250 A1 | 7/2024 | |
| WO | 2024162961 A1 | 8/2024 | |

OTHER PUBLICATIONS

PCT/US2022/012373 filed Jan. 13, 2022 International Search Report and Written Opinion dated Apr. 19, 2022.

PCT/US2022/049418 filed Nov. 9, 2022 International Search Report and Written Opinion dated Feb. 10, 2023.

U.S. Appl. No. 17/526,994, filed Nov. 15, 2021 Non-Final Office Action dated May 10, 2023.

U.S. Appl. No. 17/526,994, filed Nov. 15, 2021 Restriction Requirement dated Jan. 3, 2023.

U.S. Appl. No. 17/532,454, filed Nov. 22, 2021 Non-Final Office Action dated Mar. 22, 2023.

U.S. Appl. No. 17/542,060, filed Dec. 3, 2021 Non-Final Office Action dated Jun. 27, 2023.

U.S. Appl. No. 17/556,942, filed Dec. 20, 2021 Final Office Action dated Jul. 12, 2023.

U.S. Appl. No. 17/556,942, filed Dec. 20, 2021 Non-Final Office Action dated Jan. 31, 2023.

U.S. Appl. No. 17/561,458, filed Dec. 23, 2021 Non-Final Office Action dated Jun. 16, 2023.

U.S. Appl. No. 17/561,504, filed Dec. 23, 2021 Final Office Action dated Jul. 19, 2023.

U.S. Appl. No. 17/561,504, filed Dec. 23, 2021 Non-Final Office Action dated Mar. 14, 2023.

U.S. Appl. No. 17/863,898, filed Jul. 13, 2022 Non-Final Office Action dated Jul. 17, 2023.

U.S. Appl. No. 17/902,705, filed Sep. 2, 2022 Non-Final Office Action dated May 24, 2023.

U.S. Appl. No. 17/373,568, filed Jul. 12, 2021 Notice of Allowance dated Apr. 26, 2024.

U.S. Appl. No. 17/526,994, filed Nov. 15, 2021 Non-Final Office Action dated Apr. 22, 2024.

U.S. Appl. No. 17/542,060, filed Dec. 3, 2021 Notice of Allowance dated Jun. 3, 2024.

U.S. Appl. No. 17/556,942, filed Dec. 20, 2021 Final Office Action dated Apr. 4, 2024.

U.S. Appl. No. 17/796,604, filed Jul. 29, 2022 Notice of Allowance dated May 1, 2024.

U.S. Appl. No. 17/863,898, filed Jul. 13, 2022 Non-Final Office Action dated Mar. 11, 2024.

U.S. Appl. No. 17/902,705, filed Sep. 2, 2022 Final Office Action dated May 22, 2024.

U.S. Appl. No. 17/373,568, filed Jul. 12, 2021 Non-Final Office Action dated Nov. 9, 2023.

U.S. Appl. No. 17/526,994, filed Nov. 15, 2021 Advisory Action dated Jan. 19, 2024.

U.S. Appl. No. 17/526,994, filed Nov. 15, 2021 Final Office Action dated Oct. 24, 2023.

U.S. Appl. No. 17/532,454, filed Nov. 22, 2021 Final Office Action dated Sep. 27, 2023.

U.S. Appl. No. 17/532,454, filed Nov. 22, 2021 Notice of Allowance dated Dec. 8, 2023.

U.S. Appl. No. 17/542,060, filed Dec. 3, 2021 Non-Final Office Action dated Nov. 28, 2023.

U.S. Appl. No. 17/556,942, filed Dec. 20, 2021 Advisory Action dated Sep. 1, 2023.

U.S. Appl. No. 17/556,942, filed Dec. 20, 2021 Non-Final Office Action dated Nov. 3, 2023.

U.S. Appl. No. 17/561,458, filed Dec. 23, 2021 Final Office Action dated Sep. 12, 2023.

U.S. Appl. No. 17/561,458, filed Dec. 23, 2021 Notice of Allowance dated Dec. 6, 2023.

U.S. Appl. No. 17/561,504, filed Dec. 23, 2021 Non-Final Office Action dated Nov. 27, 2023.

U.S. Appl. No. 17/561,504, filed Dec. 23, 2021 Notice of Allowance dated Jan. 22, 2024.

U.S. Appl. No. 17/863,898, filed Jul. 13, 2022 Advisory Action dated Jan. 30, 2024.

U.S. Appl. No. 17/863,898, filed Jul. 13, 2022 Final Office Action dated Nov. 22, 2023.

U.S. Appl. No. 17/902,705, filed Sep. 2, 2022 Advisory Action dated Oct. 19, 2023.

U.S. Appl. No. 17/902,705, filed Sep. 2, 2022 Final Office Action dated Aug. 17, 2023.

U.S. Appl. No. 17/902,705, filed Sep. 2, 2022 Non-Final Office Action dated Dec. 7, 2023.

U.S. Appl. No. 17/526,994, filed Nov. 15, 2021 Final Office Action dated Nov. 19, 2024.

U.S. Appl. No. 17/556,942, filed Dec. 20, 2021 Notice of Allowance dated Jun. 26, 2024.

(56) References Cited

OTHER PUBLICATIONS

U.S. Appl. No. 17/571,254, filed Jan. 7, 2022 Restriction Requirement dated Oct. 4, 2024.
U.S. Appl. No. 17/863,898, filed Jul. 13, 2022 Advisory Action dated Oct. 28, 2024.
U.S. Appl. No. 17/863,898, filed Jul. 13, 2022 Final Office Action dated Aug. 22, 2024.
U.S. Appl. No. 17/863,898, filed Jul. 13, 2022 Non-Final Office Action dated Dec. 2, 2024.
U.S. Appl. No. 17/902,705, filed Sep. 2, 2022 Advisory Action dated Aug. 1, 2024.
U.S. Appl. No. 17/902,705, filed Sep. 2, 2022 Notice of Allowance dated Sep. 18, 2024.
U.S. Appl. No. 17/526,994, filed Nov. 15, 2021 Notice of Allowance dated Feb. 5, 2025.
U.S. Appl. No. 17/571,254, filed Jan. 7, 2022 Non-Final Office Action dated Feb. 13, 2025.
U.S. Appl. No. 18/674,694, filed May 24, 2024 Non-Final Office Action dated Mar. 3, 2025.
PCT/US2022/051431 filed Nov. 30, 2022 International Search Report and Written Opinion dated May 22, 2022.
PCT/US2023/010515 filed Jan. 10, 2023 International Search Report and Written Opinion dated Sep. 12, 2023.
PCT/US2023/012095 filed Feb. 1, 2023 International Preliminary Report on Patentability dated Jul. 31, 2025.
PCT/US2023/012095 filed Feb. 1, 2023 International Search Report and Written Opinion dated Jul. 17, 2023.
U.S. Appl. No. 17/571,254, filed Jan. 7, 2022 Final Office Action dated Aug. 13, 2025.
U.S. Appl. No. 17/701,395, filed Mar. 22, 2022 Non-Final Office Action dated Jun. 3, 2025.

U.S. Appl. No. 17/863,898, filed Jul. 13, 2022 Advisory Action dated Aug. 6, 2025.
U.S. Appl. No. 17/863,898, filed Jul. 13, 2022 Final Office Action dated Jun. 3, 2025.
U.S. Appl. No. 18/674,694, filed May 24, 2024 Notice of Allowance dated Jun. 23, 2025.
EP 25167903.1 filed Apr. 2, 2025 Extended European Search Report dated Oct. 7, 2025.
U.S. Appl. No. 17/701,395, filed Mar. 22, 2022 Final Office Action dated Dec. 17, 2025.
U.S. Appl. No. 17/863,898, filed Jul. 13, 2022 Notice of Allowance dated Sep. 16, 2025.
U.S. Appl. No. 18/622,604, filed Mar. 29, 2024 Non-Final Office Action dated Oct. 2, 2025.
U.S. Appl. No. 18/882,228, filed Sep. 11, 2024 Non-Final Office Action dated Oct. 1, 2025.
U.S. Appl. No. 18/899,727, filed Sep. 27, 2024 Notice of Allowance dated Sep. 30, 2025.
U.S. Appl. No. 17/571,254, filed Jan. 7, 2022 Non-Final Office Action dated Mar. 25, 2026.
U.S. Appl. No. 17/701,395, filed Mar. 22, 2022 Advisory Action dated Feb. 19, 2026.
U.S. Appl. No. 17/701,395, filed Mar. 22, 2022 Notice of Allowance dated Apr. 15, 2026.
U.S. Appl. No. 17/873,923, filed Jul. 26, 2022 Non-Final Office Action dated Jan. 27, 2026.
U.S. Appl. No. 18/622,604, filed Mar. 29, 2024 Final Office Action dated Apr. 7, 2026.
U.S. Appl. No. 18/706,737, filed May 1, 2024 Non-Final Office Action dated Mar. 13, 2026.
U.S. Appl. No. 18/882,228, filed Sep. 11, 2024 Notice of Allowance dated Feb. 5, 2026.
U.S. Appl. No. 18/899,727, filed Sep. 27, 2024 Notice of Allowance dated Mar. 19, 2026.

* cited by examiner

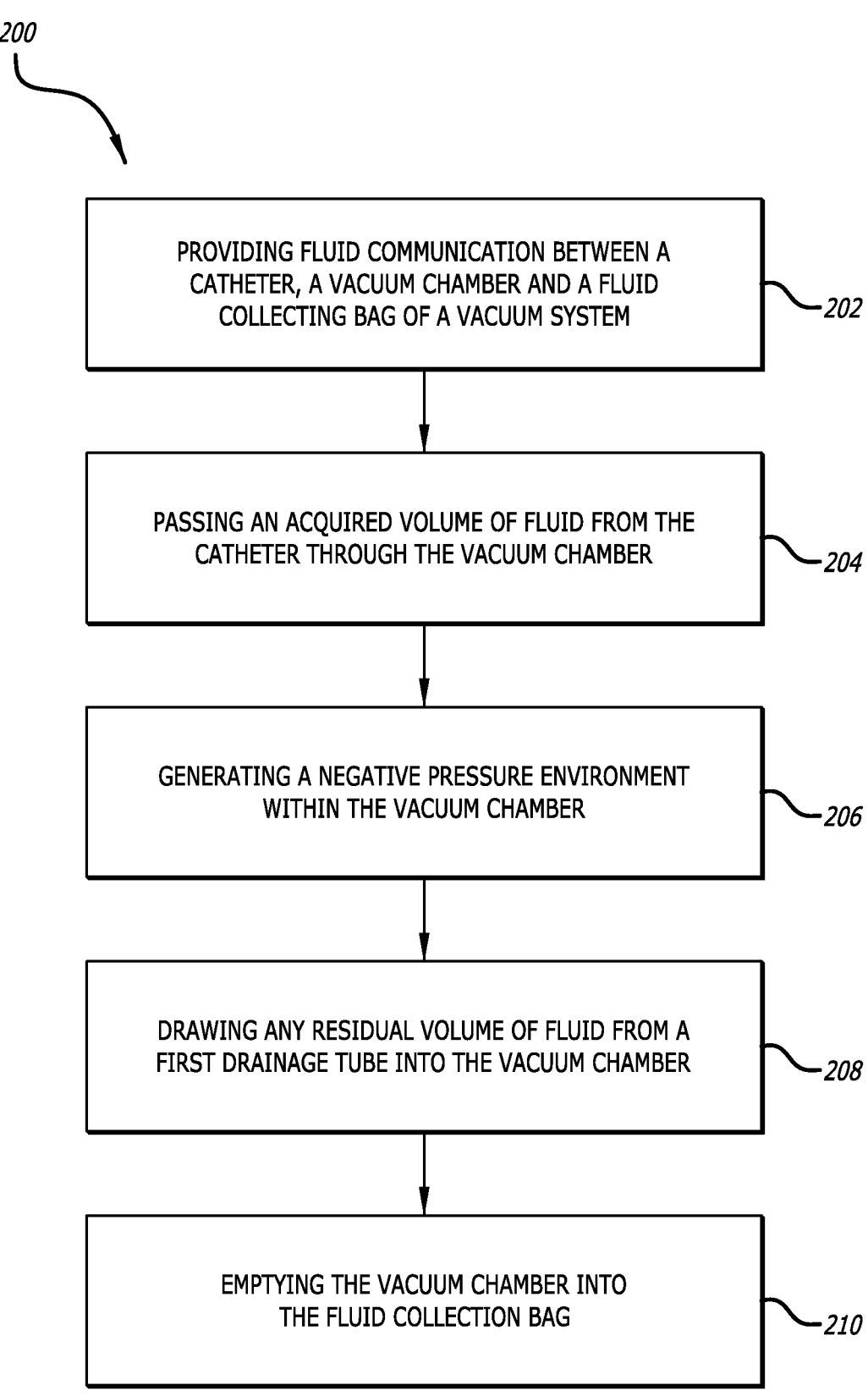

*200*

PROVIDING FLUID COMMUNICATION BETWEEN A
CATHETER, A VACUUM CHAMBER AND A FLUID
COLLECTING BAG OF A VACUUM SYSTEM
*202*

PASSING AN ACQUIRED VOLUME OF FLUID FROM THE
CATHETER THROUGH THE VACUUM CHAMBER
*204*

GENERATING A NEGATIVE PRESSURE ENVIRONMENT
WITHIN THE VACUUM CHAMBER
*206*

DRAWING ANY RESIDUAL VOLUME OF FLUID FROM A
FIRST DRAINAGE TUBE INTO THE VACUUM CHAMBER
*208*

EMPTYING THE VACUUM CHAMBER INTO
THE FLUID COLLECTION BAG
*210*

*FIG. 6*

VACUUM SYSTEM TO CLEAR STANDING COLUMN OF FLUID

PRIORITY

This application is a U.S. national stage application of International Application No. PCT/US2022/012373, filed Jan. 13, 2022, which claims the benefit of priority to U.S. Provisional Application No. 63/141,302, filed Jan. 25, 2021, each of which is incorporated by reference in its entirety into this application.

BACKGROUND

Urine transport from a patient to a urine collecting bag may be facilitated by gravity. In some configurations, the collecting bag and drainage tubing connecting to the patient must be sloped downward with the bag at a lower height than the patient's bladder. However due to normal patient movement over time, the drainage tubing may incur tubing loops that lead to a volume of urine that is retained within the tubing and does not reach the bag. The retained urine within the tubing can lead to inaccurate urine output measurements and increased pressure on the patients' bladder to expel the urine into the bag. The increased pressure can lead to injury if the pressure is not alleviated in a timely manner. Current methods to clear the retained urine within the tubing require clinicians to lift the tubing to push the fluid towards the bag. It would be beneficial to the patient and the clinician to have a system that ensures all urine from the bladder gets transported to the collecting bag within additional steps. Disclosed herein is an apparatus, a system and method of use that address the foregoing.

SUMMARY

Disclosed herein is a vacuum system including, in some embodiments, a vacuum chamber in fluid communication with each of a catheter, a suction tube, and a fluid collecting bag, the vacuum chamber having a proximal opening covered by a lid; a lateral opening coupled to a first drainage tube configured to receive a volume of fluid; and a distal opening coupled to a proximal opening of a valve.

In some embodiments, the valve includes a one way ball valve.

In some embodiments, a distal opening of the one way ball valve is coupled to a second drainage tube in fluid communication with the fluid collecting bag.

In some embodiments, the first drainage tube in fluid communication with the catheter.

In some embodiments, the lid includes a suction tube attachment configured to couple with the suction tube, the suction tube in fluid communication with a motor and being configured to remove a volume of air from or insert the volume of air into the vacuum chamber.

In some embodiments, the one way ball valve includes a valve body having the proximal opening, the distal opening, a ball valve lumen having a ball valve lumen diameter, an O-ring, a ball, two or more ball stoppers and one or more fluid channels.

In some embodiments, the O-ring, the ball, the two or more ball stoppers and the fluid channels are located within the ball valve lumen.

In some embodiments, the ball, the ball stoppers, and the fluid channels are located distal the O-ring.

In some embodiments, the O-ring includes an inner ring diameter.

In some embodiments, the ball includes a ball diameter.

In some embodiments, the ball diameter is smaller than the ball valve lumen diameter but greater than the O-ring inner diameter.

In some embodiments, the lid creates an airtight seal with the vacuum chamber.

In some embodiments, the lateral opening is configured to receive a volume of fluid by gravity flow.

In some embodiments, the suction tube is configured to generate a negative pressure environment within the vacuum chamber by removing the volume of air from the vacuum chamber.

In some embodiments, the negative pressure environment draws the ball proximally to the O-ring, creating a fluid seal.

In some embodiments, the suction tube is configured to generate a regular pressure environment within the vacuum chamber by inserting the volume of air into the vacuum chamber.

In some embodiments, the regular pressure environment disengages the ball from the O-ring, allowing fluid flow through the ball valve lumen.

Also disclosed herein is a method for clearing a standing column of fluid from a drainage tube, including providing fluid communication between a catheter, a vacuum chamber, and a fluid collecting bag of a vacuum system, passing an acquired volume of fluid from the catheter through the vacuum chamber, generating a negative pressure environment within the vacuum chamber, drawing any residual volume of fluid from a first drainage tube into the vacuum chamber, and emptying the vacuum chamber into the fluid collecting bag.

In some embodiments, providing includes coupling the catheter to the vacuum chamber, coupling the vacuum chamber to a valve, and coupling the valve to the fluid collecting bag.

In some embodiments, the valve includes a one-way ball valve.

In some embodiments, passing an acquired volume of fluid includes passing an acquired volume of fluid through a first drainage tube coupled to the vacuum chamber.

In some embodiments, passing an acquired volume of fluid includes using gravity flow to pass an acquired volume of fluid.

In some embodiments, generating a negative pressure environment includes using a suction tube in fluid communication with a motor, the suction tube being coupled to a lid of the vacuum chamber and being configured to remove a volume of air from the vacuum chamber.

In some embodiments, generating a negative pressure environment includes creating a seal within the one-way ball valve, preventing fluid flow out of the vacuum chamber.

In some embodiments, drawing any residual volume of fluid from a first drainage tube into the vacuum chamber includes using the negative pressure environment to draw in any residual volume of fluid from a first drainage tube into the vacuum chamber.

In some embodiments, emptying the vacuum chamber includes breaking the seal within the one-way ball valve.

In some embodiments, breaking the seal within the one-way ball valve includes generating a regular pressure environment within the vacuum chamber.

In some embodiments, generating the regular pressure environment within the vacuum chamber includes the suction tube being configured to return the volume of air to the vacuum chamber.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 6 illustrates a flow chart of the exemplary method of clearing a standing column of fluid from a drainage tube, in accordance with some embodiments.

DESCRIPTION

Figure 1:
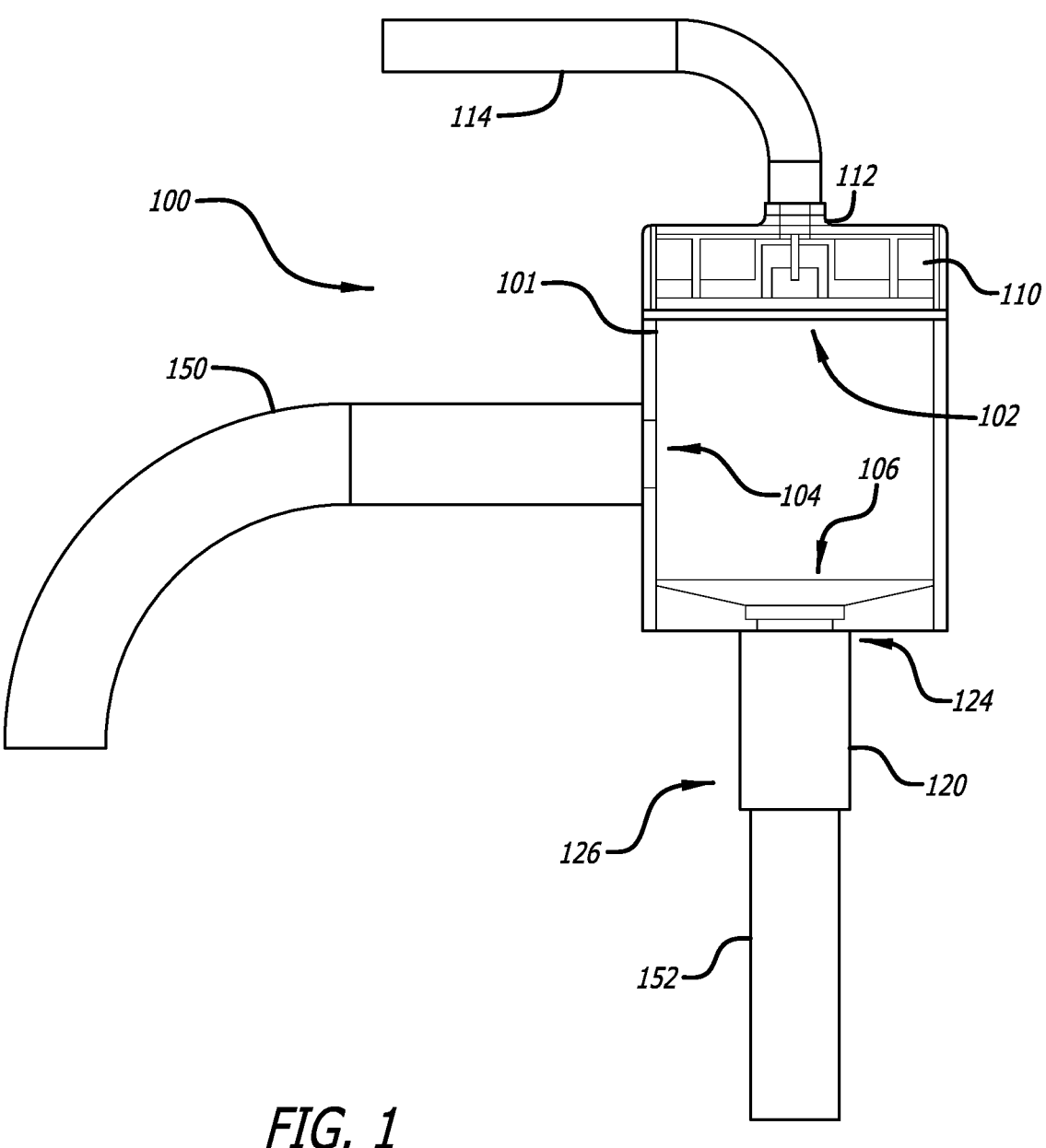
FIG. 1 illustrates a side view of a vacuum system including a vacuum chamber, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a vacuum chamber disclosed herein includes a portion of the vacuum chamber intended to be near a clinician when the vacuum chamber is used on a patient. Likewise, a "proximal length" of, for example, the vacuum chamber includes a length of the vacuum chamber intended to be near the clinician when the vacuum chamber is used on the patient. A "proximal end" of, for example, the vacuum chamber includes an end of the vacuum chamber intended to be near the clinician when the vacuum chamber is used on the patient. The proximal portion, the proximal-end portion, or the proximal length of the vacuum chamber can include the proximal end of the vacuum chamber; however, the proximal portion, the proximal-end portion, or the proximal length of the vacuum chamber need not include the proximal end of the vacuum chamber. That is, unless context suggests otherwise, the proximal portion, the proximal-end portion, or the proximal length of the vacuum chamber is not a terminal portion or terminal length of the vacuum chamber.

A fluid includes a gas, a liquid or combination of both (e.g., water vapor, a mist, droplets or the like). Fluid communication includes communication of a gas, a liquid or a combination of both.

With respect to "distal," a "distal portion" or a "distal-end portion" of, for example, a vacuum chamber disclosed herein includes a portion of the vacuum chamber intended to be near or in a patient when the vacuum chamber is used on the patient. Likewise, a "distal length" of, for example, the vacuum chamber includes a length of the vacuum chamber intended to be near or in the patient when the vacuum chamber is used on the patient. A "distal end" of, for example, the vacuum chamber includes an end of the vacuum chamber intended to be near or in the patient when the vacuum chamber is used on the patient. The distal portion, the distal-end portion, or the distal length of the vacuum chamber can include the distal end of the chamber; however, the distal portion, the distal-end portion, or the distal length of the vacuum chamber need not include the distal end of the vacuum chamber. That is, unless context suggests otherwise, the distal portion, the distal-end portion, or the distal length of the vacuum chamber is not a terminal portion or terminal length of the vacuum chamber.

Unless defined otherwise, all technical and scientific terms used herein have the same meaning as commonly understood by those of ordinary skill in the art.

FIG. 1 illustrates a side view of a vacuum system 100 including a vacuum chamber 101, in accordance with some embodiments. In some embodiments, the vacuum system 100 includes the vacuum chamber 101 in fluid communication with each of a catheter, a suction tube 114 and a fluid collecting bag. Exemplary catheters include indwelling catheters, Foley catheters, balloon catheters, peritoneal drainage catheters, or the like, and are configured to be inserted into an orifice within the body of a patient to drain a fluid therefrom. The vacuum system 100 may be configured to remove a fluid column from a drainage tube. In some embodiments as illustrated in FIG. 1, the vacuum chamber 101 may be configured to include a container configured to hold a volume of fluid. In some embodiments, the vacuum chamber 101 includes a proximal opening 102, a lateral opening 104 and a distal opening 106. In some embodiments, the proximal opening 102 may be covered by a lid 110 having a suction tube attachment 112. In some embodiments, the suction tube attachment 112 may be coupled to a suction tube 114 in fluid communication with a motor configured to remove a volume of air from or insert a volume of air into the vacuum chamber 101.

In some embodiments, the lateral opening 104 may be coupled to a first drainage tube 150. In some embodiments, the first drainage tube 150 may be coupled to a catheter configured to drain fluid from a patient. In some embodiments, the distal opening 106 may be coupled to a proximal opening 124 of a valve 120 ("valve"). As used herein, the valve includes a one way ball valve ("ball valve"). It can be appreciated that other valves are also considered including but not limited to check valves, flapper valves, clapper valves, backwater valves, duckbill valves, pneumatic non-return valves or the like. The ball valve 120 may be coupled at a distal opening 126 to a second drainage tube 152 that is in fluid communication with a fluid collecting bag. In some embodiments, the first drainage tube 150 may be configured to transport a volume of fluid from the catheter, through the vacuum chamber 101 to the fluid collecting bag. In some embodiments, the volume of fluid may include body fluids. Exemplary body fluids can include urine, blood, interstitial fluid, peritoneal fluid, saliva, mucus, or the like. In some embodiments, the suction tube 114 may be configured to generate a negative pressure environment within the vacuum chamber 101 configured to draw in a volume of fluid from the first drainage tube 150 into the vacuum chamber 101 or the suction tube 114 may be configured to generate a regular pressure environment within the vacuum chamber 101 configured to empty the vacuum chamber 101 of the volume of fluid, each in a mechanism that will be described in more detail herein.

Figure 2:
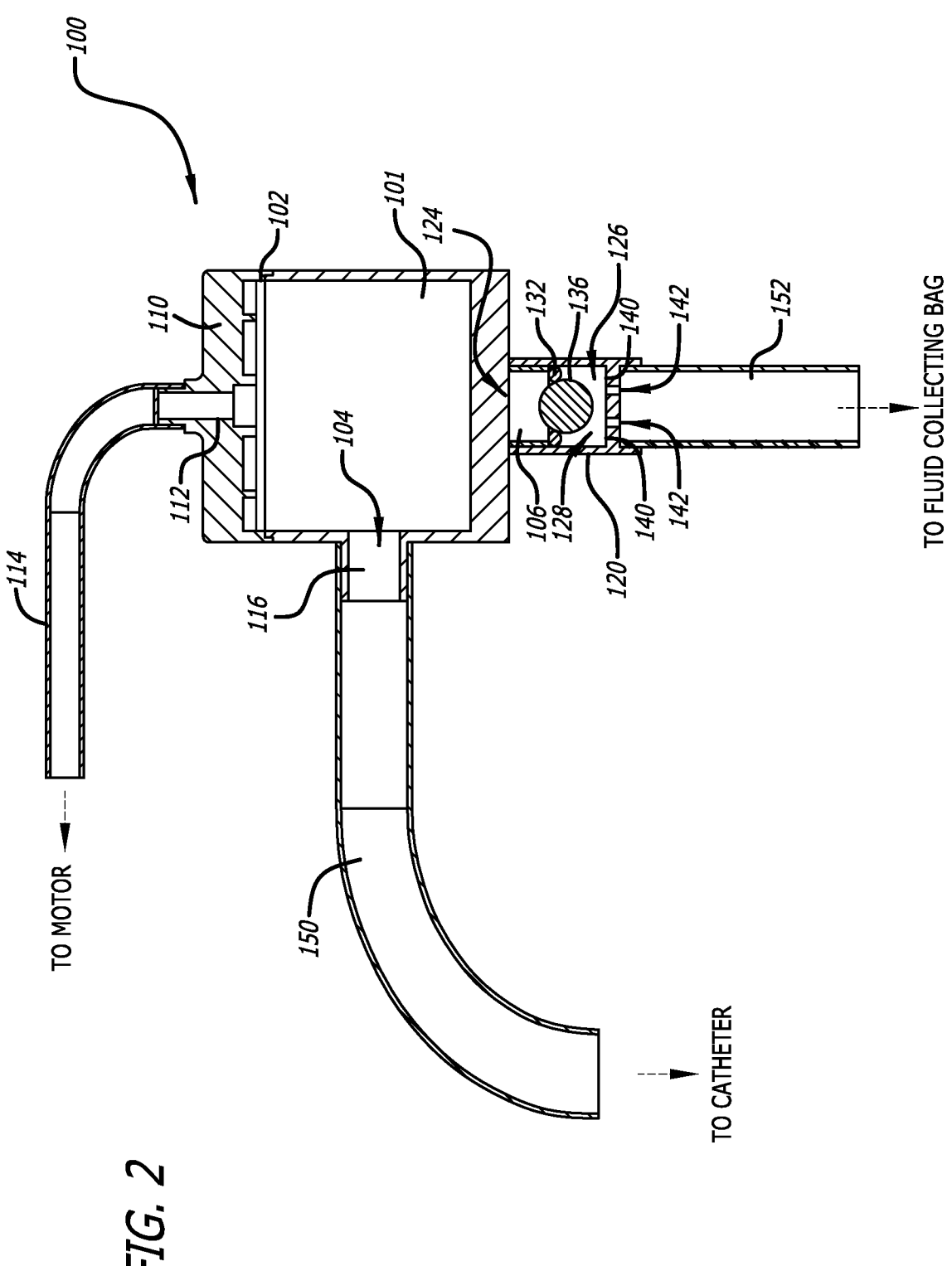
FIG. 2 illustrates a cross sectional view of the vacuum system including the vacuum chamber, in accordance with some embodiments.

FIG. 2 illustrates a cross sectional view of the vacuum system 100 including the vacuum chamber 101, in accordance with some embodiments. In some embodiments, the proximal opening 102 of the vacuum chamber 101 may be covered by the lid 110 coupled to the vacuum chamber 101. In some embodiments, the lid 110 may be coupled to the vacuum chamber 101 to create an airtight seal through a snap fit, press fit, interference fit, screw fit or the like. In some embodiments, the suction tube attachment 112 may be configured to be maintain fluid communication between the vacuum chamber 101 and the suction tube 114. In some embodiments, the vacuum chamber 101 may include a fluid intake attachment 116 on the lateral side of the vacuum chamber 101, the fluid intake attachment 116 being in fluid communication with the lateral opening 104. The vacuum chamber 101 may be configured to receive a volume of fluid through the fluid intake attachment 116 and the lateral opening 104. In some embodiments, the fluid intake attachment 116 may be configured to slidably receive thereon the first drainage tube 150. In some embodiments, the lateral opening 104 may be located anywhere between the distal opening 106 and the proximal opening 102. In some embodiments, the lateral opening 104 may be located closer to the proximal opening 102 to accommodate within the vacuum chamber 101, a larger volume of fluid or closer to the distal opening 106 to accommodate within the vacuum chamber 101, a smaller volume of fluid.

The distal opening 106 of the vacuum chamber 101 may be coupled to the proximal opening 124 of the ball valve 120. The ball valve 120 may be coupled to the vacuum chamber 101 through a press fit, a snap fit, an interference fit or the like. Other mechanisms of coupling valves to fluid containers are considered. The distal opening 126 of the ball valve 120 may be coupled to the second drainage tube 152, the second drainage tube 152 in fluid communication with the fluid collecting bag. The ball valve 120 may be configured to only allow fluid to move from the vacuum chamber 101 through the ball valve 120 to the fluid collecting bag. In some embodiments, the ball valve 120 includes the proximal opening 124, the distal opening 126 and a ball valve lumen 128 therebetween. The ball valve 120 further includes an O-ring 132, a ball 136, and two or more ball stoppers 140. The proximal opening 124 may be configured to slidably receive the distal opening 106 of the vacuum chamber 101. The distal opening 126 of the ball valve 120 may be configured to slidably receive the second drainage tube 152. The ball valve 120 may be configured to maintain fluid communication between the vacuum chamber 101 and the fluid collecting bag.

Figure 3:
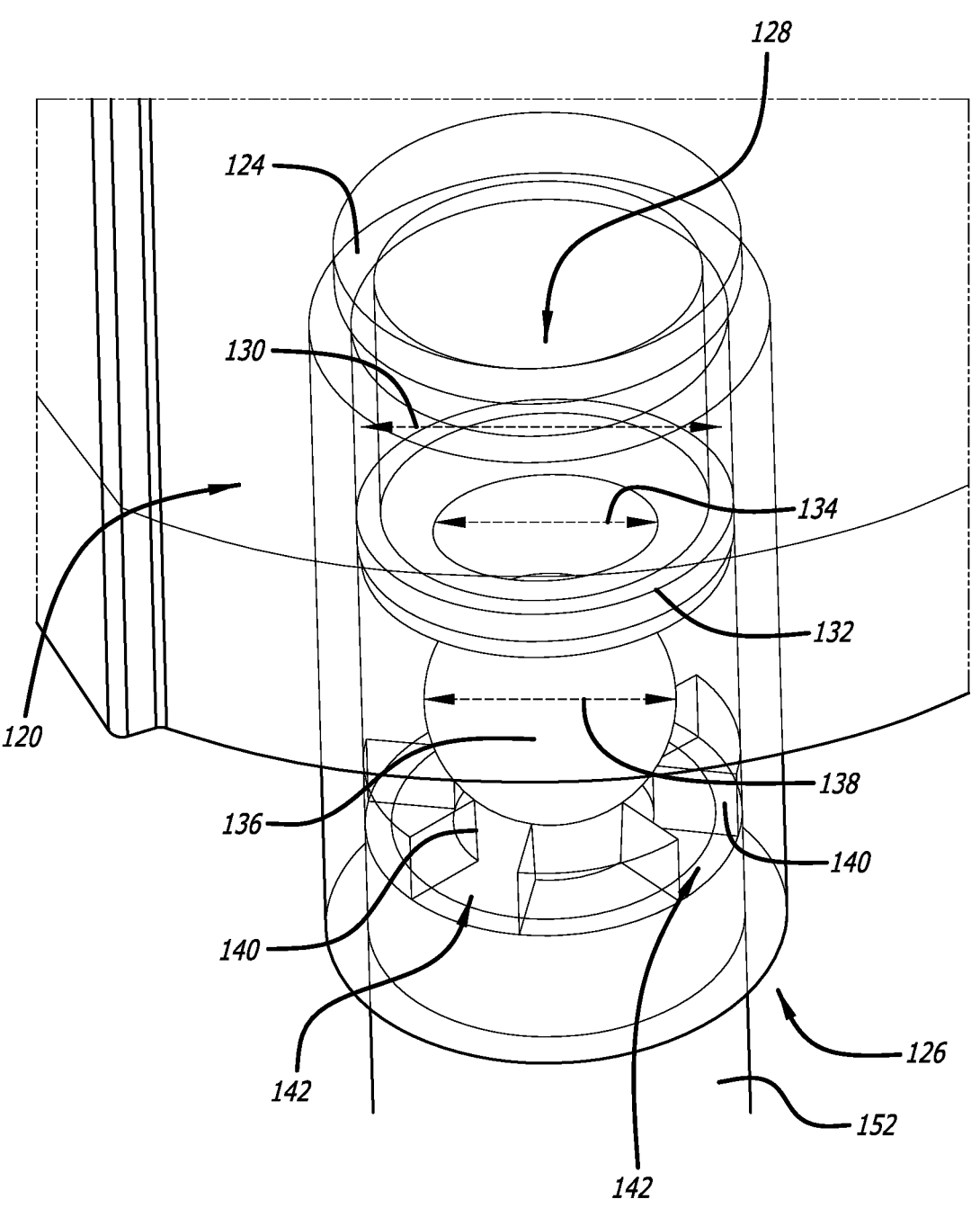
FIG. 3 illustrates a perspective view of the one way ball valve, in accordance with some embodiments.

FIG. 3 illustrates a perspective view of the ball valve 120, in accordance with some embodiments. In some embodiments, the ball valve 120 includes the ball valve body 122 having the proximal opening 124, the distal opening 126 and the ball valve lumen 128 therethrough. In some embodiments, the ball valve body 122 may be shaped in a cylinder, a rectangular prism, a triangle prism or the like. The ball valve lumen 128 includes a ball valve lumen diameter 130. The ball valve 128 further includes the O-ring 132 and the ball 136, with the O-ring 132 being proximal to the ball 136. The O-ring 132 includes an O-ring inner diameter 134. In some embodiments, the ball 136 includes a ball diameter 138 that is less than the ball valve lumen diameter 130 but greater than the O-ring inner diameter 134. In some embodiments, the ball valve lumen 128 further includes the two or more ball stoppers 140, extending radially into the ball valve lumen 128. The two or more ball stoppers 140 are located distal the ball 136. The ball 136 may be configured to freely move within the lumen 128 between the O-ring 132 and the ball stoppers 140. The ball 136 may be configured to be coupled to the O-ring 132, creating a fluid impermeable seal. The ball 136 may also be configured to rest on the ball stoppers 140, allowing fluid flow around the ball 136 and through the ball valve lumen 128. The ball stoppers 140 may be arranged to create one or more valve channels 142, configured to allow fluid flow from the ball valve lumen 128 through the distal opening 126 of the ball valve 120.

Figure 4:
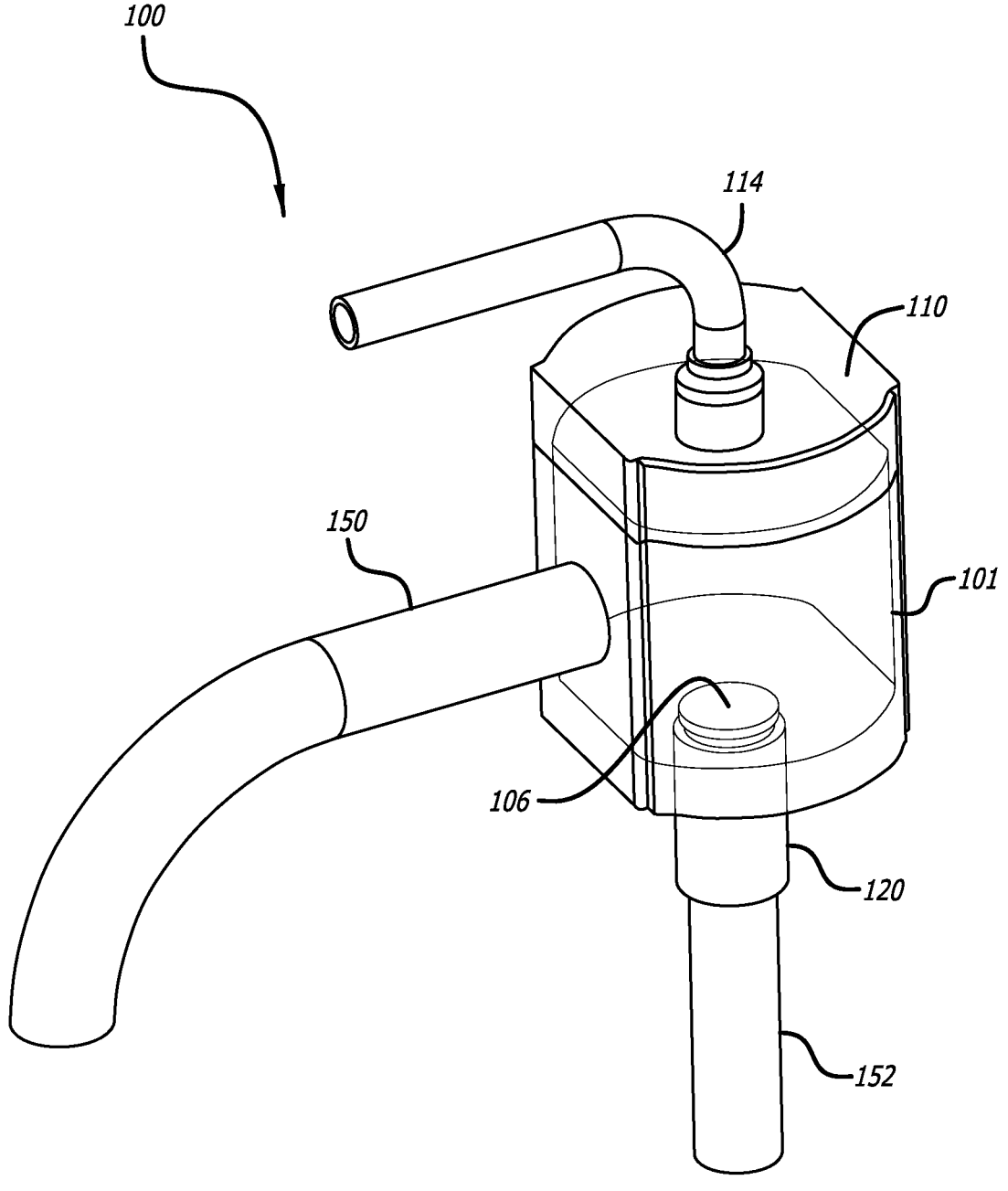
FIG. 4 illustrates a perspective view of the vacuum chamber, in accordance with some embodiments.

FIG. 4 illustrates a perspective view of the vacuum system 100 including the vacuum chamber 101, in accordance with some embodiments. In some embodiments, the vacuum chamber 101 may be coupled to a medical bed or coupled to a surface configured to maintain the orientation of the vacuum system 100 illustrated in FIG. 4. In some embodiments, the vacuum system 100 including the vacuum chamber 101 may be configured to be a stand-alone unit or coupled to additional medical devices. In some embodiments, the vacuum chamber 101 may be constructed out of synthetic polymers, thermoplastic polyurethanes or plastics including by not limited to polypropylene, polyvinyl chloride, polystyrene or the like. In some embodiments, the vacuum chamber 101 may be extruded, pressed from a sheet and folded into shape, 3D printed or the like. In some embodiments, the vacuum chamber 101 may be configured to be disposable or reusable. In some embodiments, the ball valve 120 may be configured to detachably couple to the vacuum chamber 101. In some embodiments, the ball valve 120 may be configured to be permanently coupled to the vacuum chamber 101. In some embodiments, the lid 110 may be configured to detachably couple to the vacuum chamber 101. In some embodiments, the lid 110 may be permanently coupled to the vacuum chamber 101. In some embodiments, the vacuum chamber 101 may be configured in the shape of a cylinder, a rectangular prism, a triangle prism, an irregular polygon or the like.

Figure 5A:
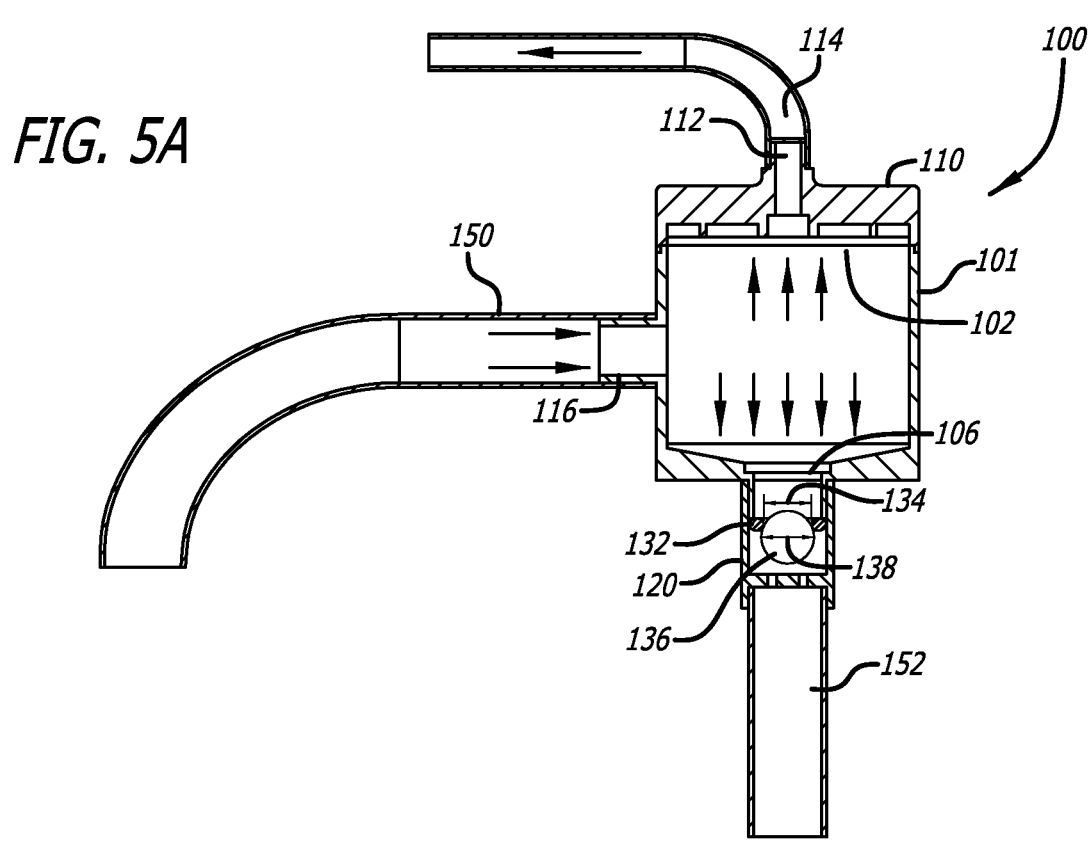
FIGS. 5A-5B illustrate an exemplary method of clearing a standing column of fluid from a first drainage tube, in accordance with some embodiments.
Figure 5B:
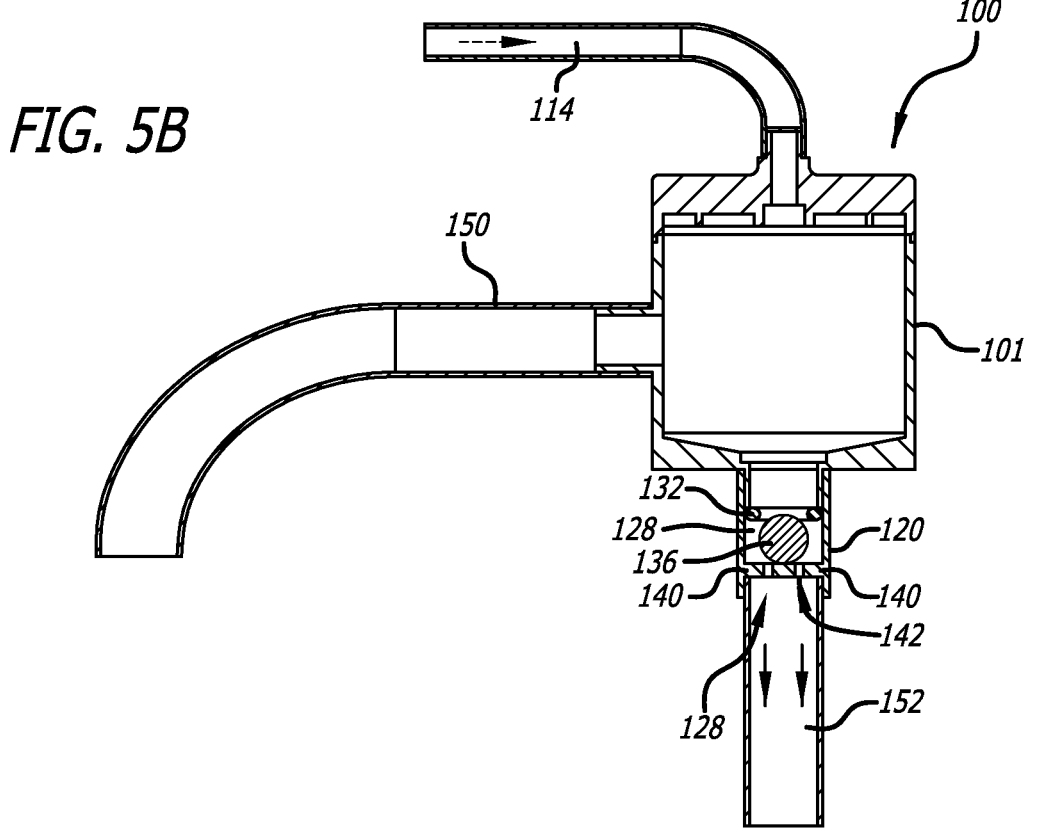

FIGS. 5A-5B illustrate an exemplary method of clearing a standing column of fluid from the first drainage tube 150, in accordance with some embodiments. As illustrated in FIG. 5A, the vacuum system 100 includes the vacuum chamber 101 in fluid communication with the suction tube 114, a catheter and a fluid collecting bag. In some embodiments, the vacuum chamber 101 may be coupled at the lateral opening 104 to the first drainage tube 150, the first drainage tube 150 being in fluid communication with a catheter. The proximal opening 102 of the vacuum chamber 101 may be covered by the lid 110 having the suction tube attachment 112. The suction tube attachment 112 may be coupled to the suction tube 114, in fluid communication with a motor configured to remove a volume of air out of the vacuum chamber 101 or input the volume of air into the vacuum chamber 101. The distal opening 106 of the vacuum chamber 101 may be coupled to the proximal end 124 of the ball valve 120. A volume of fluid may flow from the catheter, through the first drainage tube 150 coupled to the fluid intake attachment 116, through the lateral opening 104 into the vacuum chamber 101, by gravity flow. The volume of fluid may pass from the vacuum chamber 101 through the ball valve 120 into the fluid collecting bag. However, a portion of the volume of fluid may remain within the first drainage tube 150. The portion of the volume of fluid remaining within the first drainage tube 150 will be referred herein as the residual volume of fluid.

As illustrated in FIG. 5A, to remove the residual volume of fluid remaining within the first drainage tube 150, the volume of air may be removed out of the vacuum chamber 101 by way of the suction tube 114, creating a negative pressure environment within the vacuum chamber 101. The negative pressure environment within the vacuum chamber 101 draws the ball 136 in the ball valve 120 proximally towards the O-ring 132, wherein the larger ball diameter 138 creates a fluid seal between the ball 136 and the smaller inner ring diameter 134 of the O-ring 132, preventing any fluid flow through the ball valve 120. The negative pressure environment within the vacuum chamber 101 may be configured to draw into the vacuum chamber 101 the residual volume of fluid within the first drainage tube 150 that did not enter the vacuum chamber 101 by gravity flow.

As illustrated in FIG. 5B, once the first drainage tube 150 is cleared of the residual volume of fluid, the vacuum chamber 101 may be configured to be emptied into the fluid collecting bag. To empty the vacuum chamber 101, the motor may be configured insert the volume of air back into the vacuum chamber 101, creating a regular pressure environment. The regular pressure environment allows the ball 136 to break from the O-ring 132 in the ball valve 120. The breaking of the ball from the O-ring 132 breaks the fluid seal, pushing the ball 136 distally to the ball stoppers 140. The residual volume of fluid within the vacuum chamber 101 may be configured to flow out of the distal opening 106, through the ball valve lumen 128 and the valve channels 142 through the distal opening 126 into the second drainage tube 152. The regular pressure environment is an environment within the vacuum chamber 101 wherein fluid may freely flow through the vacuum chamber 101 to the fluid collecting bag by gravity flow.

In some embodiments, as the vacuum chamber 101 is filled with residual volume of fluid, the pressure on the ball 136 in the ball valve 120 increases until the fluid seal is broken, pushing the ball 136 distally from the O-ring 132 until the ball 136 rests on the two or more ball stoppers 140. The residual volume of fluid may be configured to flow from the vacuum chamber 101, through the ball valve lumen 128, around the ball 136 and through the distal opening of the ball valve 120 into the second drainage tube 152. Once the residual volume of fluid is drained from the vacuum chamber 101, the vacuum chamber 101 may be configured to have the negative pressure environment or regular pressure environment at a user's discretion. The vacuum system 100 is a closed system wherein the same volume of air removed from the vacuum chamber 101 to create the negative pressure environment is returned to the vacuum chamber 101 to create the regular pressure environment. Advantageously, the closed system ensures no contamination of the collected fluid occurs. Furthermore, the negative pressure environment causes the ball valve 120 to be sealed, preventing the fluid collecting bag from deflating from the negative pressure within the vacuum chamber 101.

FIG. 6 illustrates a flow chart of the exemplary method of clearing a standing column of fluid from the first drainage tube 150, in accordance with some embodiments. In some embodiments, the method 200 includes providing fluid communication between the vacuum system 100, the vacuum system 100 including the catheter, the vacuum chamber 101 and the fluid collecting bag (block 202). In some embodiments providing includes coupling the catheter to the lateral opening 104 of the vacuum chamber 101, coupling the distal opening 106 of the vacuum chamber 101 with the proximal opening 124 of the ball valve 120 and coupling the distal opening 126 of the ball valve 120 to the fluid collecting bag. The method 200 further includes passing an acquired volume of fluid from the catheter through the vacuum chamber 101 (block 204). In some embodiments, passing includes using gravity flow to pass the acquired volume of fluid through the vacuum chamber 101. In some embodiments, passing includes passing the acquired volume of fluid through the first drainage tube 150 coupled to the vacuum chamber 101 at the lateral opening 104.

The method 200 further includes generating a negative pressure environment within the vacuum chamber 101 (block 206). In some embodiments, creating a negative pressure environment includes the lid 110 of the vacuum chamber 101 being coupled to the suction tube 114. In some embodiments, the suction tube 114 is in fluid communication with a motor. The suction tube 114 may be configured to remove a volume of air from the vacuum chamber 101. In some embodiments, creating a negative pressure environment within the vacuum chamber 101 includes creating a seal within the ball valve 120 to prevent fluid flow out of vacuum chamber 101. In some embodiments, the seal within the ball valve 120 is created by the negative pressure environment within the vacuum chamber 101 drawing the ball 136 up to the O-ring 132 creating the seal. The ball diameter 138 being larger than the O-ring inner diameter 134 creates the seal within the ball valve lumen 128.

The method 200 further includes drawing any residual volume of fluid into the vacuum chamber (block 208). In some embodiments, a portion of the volume of fluid may not pass through the vacuum chamber 101 by gravity flow but may reside within the first drainage tube 150. In some embodiments, drawing includes using the negative pressure environment to draw the residual volume of fluid from the first drainage tube 150 into the vacuum chamber 101. The method 200 further includes emptying the vacuum chamber 101 into the fluid collecting bag (block 210). In some embodiments, emptying the vacuum chamber 101 includes breaking the seal within the ball valve 120. In some embodiments, breaking the seal within the ball valve 120 includes generating a regular pressure environment within the vacuum chamber 101. In some embodiments, generating a regular pressure environment allows the ball 136 to break from the O-ring 132 causing fluid flow of the residual volume of fluid to pass through the ball valve lumen 128 into the fluid collecting bag. In some embodiments, creating a regular pressure environment within the vacuum chamber 101 includes the suction tube 114 being configured to return the volume of air back into the vacuum chamber 101 to create the regular pressure environment within the vacuum chamber 101.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A vacuum system, comprising:
a vacuum chamber in fluid communication with each of:
a catheter coupled with the vacuum chamber at a lateral opening disposed on a lateral side of the vacuum chamber,
a suction tube coupled with the vacuum chamber at a proximal opening disposed on a top side of the vacuum chamber, and
a fluid collecting bag coupled with the vacuum chamber at a distal opening disposed on a bottom side of the vacuum chamber,
wherein:
the lateral opening is disposed between the proximal opening and the distal opening,
the vacuum chamber remains in continuous fluid communication with the catheter and the suction tube, and
the suction tube is coupled to a motor configured to provide a change in air pressure within the vacuum chamber; and
a valve configured to control a fluid flow between the vacuum chamber and the fluid collecting bag;
wherein:
whenever an atmospheric pressure is present in the vacuum chamber, the valve is disposed in an open configuration such that fluid is allowed to continuously flow from the vacuum chamber into the fluid collecting bag, and
a negative air pressure applied to the vacuum chamber through the suction tube transitions the valve to a closed configuration to prevent the fluid flow from the fluid collecting bag into the vacuum chamber and draws a fluid flow from the catheter into the vacuum chamber.

2. The vacuum system according to claim 1, wherein the valve includes a one way ball valve.

3. The vacuum system according to claim 2, wherein the one way ball valve includes a valve body having a first opening coupled to the vacuum chamber, a second opening coupled to the fluid collecting bag, a ball valve lumen extending therethrough and defining a ball valve lumen diameter, an O-ring, a ball, two or more ball stoppers and one or more fluid channels.

4. The vacuum system according to claim 3, wherein the O-ring, the ball, the two or more ball stoppers and the one or more fluid channels are located within the ball valve lumen.

5. The vacuum system according to claim 4, wherein the ball, the two or more ball stoppers, and the one or more fluid channels are located between the fluid collecting bag and the O-ring.

6. The vacuum system according to claim 5, wherein the O-ring includes an inner ring diameter.

7. The vacuum system according to claim 6, wherein the ball includes a ball diameter.

8. The vacuum system according to claim 7, wherein the ball diameter is smaller than the ball valve lumen diameter but greater than the inner ring diameter of the O-ring.

9. The vacuum system according to claim 8, wherein the motor and the suction tube are configured to generate the negative air pressure within the vacuum chamber by removing a volume of first air from the vacuum chamber.

10. The vacuum system according to claim 9, wherein the negative air pressure draws the ball towards the O-ring, engaging the O-ring and creating a fluid tight seal therebetween.

11. The vacuum system according to claim 10, wherein the motor and the suction tube are configured to generate the atmospheric pressure within the vacuum chamber by adding the volume of first air back into the vacuum chamber.

12. The vacuum system according to claim 11, wherein the atmospheric pressure disengages the ball from the O-ring, allowing fluid flow through the ball valve lumen.

13. The vacuum system according to claim 1, wherein the vacuum system is configured to drain the fluid via gravity from the vacuum chamber into the fluid collecting bag when the atmospheric pressure is applied to the vacuum chamber.

14. The vacuum system according to claim 1, wherein the catheter is one of a Foley catheter, balloon catheter, or a peritoneal drainage catheter configured to drain the fluid from a body of a patient.

15. The vacuum system according to claim 1 wherein the suction tube is in fluid communication with the motor that is configured to remove a volume of air from or add the volume of air into the vacuum chamber.

16. The vacuum system according to claim 1, wherein the vacuum chamber includes a lid that creates an airtight seal with the vacuum chamber.

17. The vacuum system according to claim 1, wherein the vacuum chamber is configured to receive a volume of fluid from the catheter, and drain the volume of fluid via gravity to the fluid collecting bag.

18. A method for clearing a standing column of fluid from a drainage tube, comprising:
providing a vacuum chamber in fluid communication with the drainage tube coupled with the vacuum chamber at a lateral opening disposed on a lateral side of the vacuum chamber, a suction tube coupled with the vacuum chamber at a proximal opening disposed on a top side of the vacuum chamber, and a fluid collecting bag coupled with the vacuum chamber at a distal opening disposed on a bottom side of the vacuum chamber,
wherein:
the lateral opening is disposed between the proximal opening and the distal opening, and
the vacuum chamber remains in continuous fluid communication with the drainage tube and the suction tube;
passing a first volume of fluid from the drainage tube into the vacuum chamber;
generating a negative pressure within the vacuum chamber by activating a motor coupled with the suction tube, the motor configured to draw air out of the vacuum chamber through the suction tube to define the negative pressure within the vacuum chamber;
transitioning a valve to a closed position, the valve controlling fluid communication between the vacuum chamber and the fluid collecting bag;
drawing a second volume of fluid from the drainage tube into the vacuum chamber; and

transitioning the valve to an open position to empty at least the second volume of fluid from the vacuum chamber into the fluid collecting bag by generating an atmospheric pressure within the vacuum chamber, wherein whenever the atmospheric pressure is present in the vacuum chamber, the valve is disposed in the open position such that fluid is allowed to continuously flow from the vacuum chamber into the fluid collecting bag.

19. The method according to claim 18, wherein at least a portion of the first volume of fluid transitions to the fluid collecting bag before the motor generates the negative pressure within the vacuum chamber.

20. The method according to claim 18, wherein the valve includes a one way ball valve.

21. The method according to claim 18, wherein the drainage tube is in fluid communication with a catheter.

22. The method according to claim 18, wherein the first volume of fluid flows via gravity from the drainage tube into the vacuum chamber.

23. The method according to claim 18, wherein the motor and the suction tube generate the negative pressure by removing a volume of air from the vacuum chamber.

24. The method according to claim 18, wherein transitioning the valve to the closed position includes creating a fluid tight seal within the valve, preventing a fluid flow from the fluid collecting bag into the vacuum chamber.

25. The method according to claim 24, wherein transitioning the valve to the open position further includes generating the atmospheric pressure within the vacuum chamber.

26. The method according to claim 25, wherein generating the atmospheric pressure within the vacuum chamber further includes breaking the fluid tight seal within the valve.

27. The method according to claim 26, wherein breaking the fluid tight seal further includes disengaging a ball from an O-ring.

28. The method according to claim 25, wherein generating the atmospheric pressure within the vacuum chamber includes adding a volume of air to the vacuum chamber.

* * * * *